(12) United States Patent
Gillet et al.

(10) Patent No.: US 6,538,141 B1
(45) Date of Patent: Mar. 25, 2003

(54) METHOD FOR PREPARING NITROXIDES

(75) Inventors: Jean-Philippe Gillet, Brignais (FR); Olivier Guerret, Marcy l'Etoile (FR); Jean-Pierre Lascombe, La Mulatiere (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/869,798

(22) PCT Filed: Dec. 22, 1999

(86) PCT No.: PCT/FR99/03254

§ 371 (c)(1), (2), (4) Date: Sep. 24, 2001

(87) PCT Pub. No.: WO00/40550

PCT Pub. Date: Jul. 13, 2000

(30) Foreign Application Priority Data

Jan. 8, 1999 (FR) .............................................. 99 00128

(51) Int. Cl.⁷ .................... A61K 213/72; C07D 295/03; C07D 295/033; C07F 9/44; C07C 291/02

(52) U.S. Cl. ........................ 546/304; 546/184; 546/186; 544/106; 564/15; 564/297; 564/298

(58) Field of Search .................................. 546/184, 186, 546/304; 544/106; 564/15, 297, 298

(56) References Cited

U.S. PATENT DOCUMENTS 4,665,185 A * 5/1987 Winter et al. ................ 546/184
4,845,090 A 7/1989 Heinz et al.
5,087,752 A * 2/1992 Murray et al. ......... 252/182.12

FOREIGN PATENT DOCUMENTS

EP 0488403 * 3/1992
FR 2036557 12/1970
GB 1199351 * 7/1970
WO 9624620 8/1996

* cited by examiner

*Primary Examiner*—Alan L. Rotman
*Assistant Examiner*—Rita Desai
(74) *Attorney, Agent, or Firm*—Millen, White, Zelano & Branigan, P.C.

(57) ABSTRACT

The invention concerns a method for preparing nitroxides, which consists in oxidising, in a two-phase medium, using an aliphatic peroxide, secondary amines with steric hindrance or having a —CH in the nitrogen atom α.

19 Claims, No Drawings

METHOD FOR PREPARING NITROXIDES

The present invention relates to a process for preparing secondary amine N-oxide radicals by oxidizing the corresponding secondary amines.

Secondary amine N-oxide radicals, referred to hereinbelow as nitroxides, are free radicals containing an unpaired electron. These nitroxide radicals may be used as stabilizers for organic polymers, in particular to inhibit the thermal and light-mediated degradation of polyolefins (U.S. Pat. No. 3,431,233) and of PVC (U.S. Pat. No. 3,547,874). They are also used as spin labels for studying biological compounds and as free-radical polymerization regulators (Georges, M. K. et al. Macromolecules 1993, 26, 2987).

The main methods for preparing nitroxides are the oxidation of hydroxylamines and the oxidation of secondary amines, this second method being the one which is most commonly used industrially.

The methods for obtaining nitroxide radicals by oxidizing the corresponding secondary amines have been widely described.

Among these methods, mention will be made of those which use aqueous hydrogen peroxide solution in the presence of catalysts such as phosphotungstic acid (Briére R. et al., Bulletin de la Société Chimique de France, 1965, pages 3273–3282), alkaline-earth metal salts (EP 0 574 607), $NaHCO_3$ or $Na_2CO_3$ (Levina et al., Dokl. Akad. Nauk. SSSR 1981, 261(1), 109–110), EDTA combined with $WO_4Na_2$ (Zakizewski J., J. Prakt. Chem. 1985, 327(6), 1011–1014).

In all these methods, the oxidation reaction takes place in water or a water/alcohol mixture at temperatures of between 60 and 100° C.

Although they use an inexpensive oxidizing agent—$H_2O_2$—these methods are applicable only to amine/nitroxide couples that are sufficiently water-soluble. They also have drawbacks residing especially in long reaction times and in the impossibility of recycling the catalytic system, thus making it necessary to wash the product and treat the effluents before removing them.

In addition, these methods are not general since the temperatures used, generally high, make it difficult, if not impossible, to isolate certain nitroxides that are readily overoxidizable.

Other methods for oxidizing secondary amines to nitroxides have been proposed.

Thus, patent U.S. Pat. No. 4,665,185 discloses a process for oxidizing cyclic secondary amine, which consists in reacting said amine in an inert organic solvent, with an organic hydroperoxide such as tert-butyl hydroperoxide, in the presence of catalytic amounts of a metal carbonyl ($Mo(CO)_6$), a metal oxide ($MoO_3$), a metal acetylacetonate or a metal alkoxide ($Ti(OiPr)_4$), the metal of which belongs to one of the groups IVB, VB, VIB, VIB and VIII of the Periodic Table, at a temperature ranging from 0° C. to 200° C.

The reaction times are shorter, but the problem of recovering the catalyst still remains. The products must be purified and the effluents treated.

Another method for oxidizing secondary amine consists in reacting said secondary amine with dimethyldioxirane (DMD) in the absence of catalysts (U.S. Pat. No. 5 087 752).

DMD, which is not commercially available, is prepared by oxidizing acetone either with Oxone® which is a potassium monoperoxysulsulfate, or more rarely with Caro's acid which is an $H_2SO4/H_2SO_5$ mixture.

This powerful oxidizing agent gives high yields of nitroxides. However, its highly explosive nature makes its preparation very random and is unacceptable for industrial use.

Furthermore, to obtain DMD, it is necessary to use the Oxone® in excess in basic medium, which generates a large amount of sulfate as effluent.

Perbenzoic acids such as meta-chloroperbenzoic acid (Journal of American Chemical Society, 1967, 89(12) 3055–3056) or para-nitropebenzoic acid (Rassat A. et al. Bulletin de la Société Chimique de France, 1965, 3283–3290) dissolved in organic solvents such as methylene chloride, allow many secondary amines to be oxidized efficiently to nitroxides.

However, the cost and the benzoic acids they generate make them unsuitable for use on an industrial scale.

It has now been found that nitroxides can be obtained according to a process which avoids the abovementioned drawbacks, which consists in oxidizing secondary amines using aliphatic peracids in an organic solvent/water two-phase medium in which the aqueous phase is maintained at a pH ranging from 4 to 12.

One subject of the present invention is thus a process for preparing secondary amine N-oxide radicals (nitroxide radicals) from the corresponding secondary amines, characterized in that the following steps are carried out:

a/ the secondary amine is dissolved with a water-immiscible organic solvent, and water is then added, b/ an amount of aliphatic peracid in a peracid/secondary amine molar ratio ranging from 1.5 to 2.5 and preferably ranging from 1.5 to 2, and an amount of an aqueous basic solution sufficient to give the aqueous phase or the two-phase medium a pH ranging from 4 to 12, are then added simultaneously and with vigorous stirring to the two-phase medium thus obtained, at a temperature of between −10° C. and +40° C., until conversion of the secondary amine is complete, and then c/ the organic phase is recovered by simple separation of the phases by settling, and the nitroxide is isolated by evaporating the organic solvent under reduced pressure.

According to the present invention, the organic solvent must be water-immiscible, inert towards the reagents and products and must have good solvent power for the reagents and products obtained.

By way of illustration of such organic solvents which may be used according to the present invention, mention will be made of aliphatic or cycloaliphatic hydrocarbons such as pentane, hexane, heptane, decane, cyclohexane and cyclododecane; aromatic hydrocarbons such as benzene, toluene and xylenes; chlorinated hydrocarbons such as methylene chloride, 1,2-dichloroethane, chloroform and chlorobenzene; aliphatic acid esters such as ethyl acetate, ethyl propionate or a mixture of at least two of the above-mentioned solvents.

By way of illustration of aliphatic peracids which may be used according to the present invention, mention will be made of peracetic acid, perpropionic acid and perbutanoic acid.

Peracetic acid or perpropionic acid will preferably be used.

The process of the present invention thus consists in dissolving, with stirring, the secondary amnine in water-immiscible organic solvent which is inert towards said secondary amine and the reagents used.

The amount of organic solvent used depends on the solubility of said secondary amine in said solvent.

This amount of organic solvent is not critical and may vary within a wide range. However, for economic reasons and out of concern for the environment, a person skilled in the art will make efforts to select an organic solvent (or a mixture of solvents) so as to use only minimum amounts to dissolve the secondary amine.

Water is added to the organic solution, with stirring, followed by simultaneous addition to the two-phase medium obtained, with vigorous stirring, of the aliphatic peracid, generally dissolved in the corresponding aliphatic acid, in a peracid/secondary amine molar ratio as defined above and a sufficient amount of an aqueous basic solution of a carbonate or hydrogen carbonate of an alkali metal or of an alkaline-earth metal so that the pH of the aqueous solution of the two-phase medium is maintained at a value ranging from 4 to 12 and preferably ranging from 5 to 9.

According to the present invention, an aqueous basic solution of an alkali metal carbonate or hydrogen carbonate will preferably be used.

By way of illustration of alkali metal carbonates or hydrogen carbonates which may be used according to the present invention, mention will be made of $NaHCO_3$, $KHCO_3$, $K_2CO_3$ and $Na_2CO_3$.

Ammoniacal solutions may also be used.

The weight concentration of the aqueous solutions of alkali metal or alkaline-earth metal carbonates or hydrogen carbonates is set by the solubility limit of these species in water. Efforts will be made to use solutions that are as concentrated as possible.

The oxidation reaction of the secondary amine to nitroxide according to the scheme:

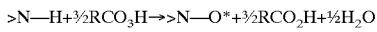

is carried out at a temperature ranging from −10° C. to +40° C. and preferably ranging from −5° C. to +30° C. until the secondary amine is completely converted. The reaction progress may be monitored by analytical methods such as chemical assay of the peracid used according to methods known to those skilled in the art (assay with sulfite and with $Ce^{4+}$) and gas chromatography.

The process is preferably performed at atmospheric pressure. Once the reaction is complete, the organic phase is recovered, generally by simple separation of the phases by settling. This organic phase may optionally be washed with a demineralized water and then dried.

The nitroxide formed is isolated by evaporating the organic solvent under reduced pressure. If necessary, the purity of the nitroxide may be improved by distillation under reduced pressure or by recrystallization. The nitroxides may be identified by elemental analysis, HPLC, IR, EPR and mass spectrometry (MS).

According to the process of the invention, the oxidation reaction of secondary amines to nitroxides has the advantage of being carried out with inexpensive, commercially available oxidizing agents, under mild conditions, quickly and in high yields.

In addition, the nitroxides obtained are easy to purify and the effluents (organic acid salts) may optionally be upgraded.

The process for oxidizing secondary amines to nitroxides according to the invention has the advantage or being applicable to secondary amines (or secondary polyamines) that are sterically hindered or to those containing a —CH α to the nitrogen atom.

In the present case, the expression "sterically hindered secondary amines" denotes amines which comprise at least one unit (A) as described below:

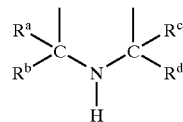

in which $R^a$, $R^b$, $R^c$ and $R^d$, which may be identical or different, represent a linear or branched alkyl radical containing a number of carbon atoms ranging from 1 to 10, or $R^a$ and $R^b$ form with the carbon atom which bears them, or $R^c$ and $R^d$ form with the carbon atom which bears them, a cycloalkyl containing a number of carbon atoms ranging from 3 to 10 or a spiran, cholestane or androstane residue.

Thus, the oxidation process of the present invention makes it possible to oxidize into nitroxide sterically hindered secondary amines comprising at least one unit (A) or secondary amines containing at least one-CH a to the nitrogen atom, chosen from the compounds represented by the following formulae, in which $R^a$, $R^b$, $R^c$ and $R^d$ have the meanings mentioned above:

the compounds of formula (I):

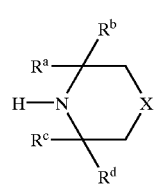

in which X represents a divalent radical chosen from the following radicals:

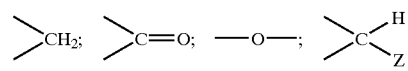

in which Z represents a monovalent residue chosen from —CN, —NHR, —OR, —N=C(R)$_2$ in which R represents a hydrogen atom, a linear or branched alkyl radical containing a number of carbon atoms ranging from 1 to 10, a benzyl radical, a phenyl radical, —CN, —C(O)R$^1$; C=N—R$^1$, C(OR$^1$)$_2$ in which R$^1$ has the same meaning as R;

the compounds of formula (II):

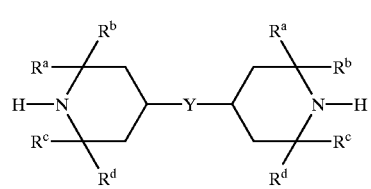

in which Y represents a divalent residue chosen from:
- —OC(O)—(CR$^2$R$^3$)$_n$—C(O) O—,
- —NH—(CR$^2$R$^3$)$_n$NH—,
- —NHC(O)—(CR$^2$R$^3$)$_n$—C(O)NH,
- —S—, —O—, R$^2$ and R$^3$, which may be identical or different, represent a hydrogen atom or a linear or branched alkyl radical containing a number of carbon atoms ranging from 1 to 10, and n represents an integer ranging from 0 to 20;

the compounds of formula (III):

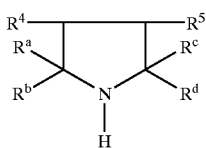
(III)

in which $R^4$ represents a hydrogen atom or a linear or branched alkyl radical containing a number of carbon atoms ranging from 1 to 10, and $R^5$ represents a hydrogen atom, $—CH_3$, $—C_2H_5$, $—CH_2OH$, $—C(O)NH_2$, $—OH$ or $—CHO$;

the compounds of formula (IV):

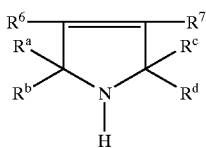
(IV)

in which $R^6$ has the same meaning as $R^4$ and $R^7$ has the same meaning as $R^5$ the 1,1,3,3-tetramethylpyrrolopoyridines of formula (V):

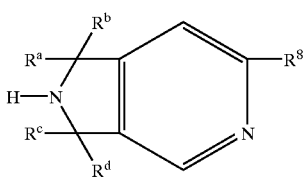
(V)

and the 1,1,3,3-tetramethyl-2,3-dihydroisoindoles of formula (VI):

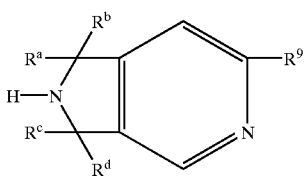
(VI)

in which $R^8$ and $R^9$ represent a hydrogen atom or a linear or branched alkyl radical containing a number of carbon atoms ranging from 1 to 10;

the compounds of formula (VII):

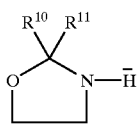
(VII)

in which $R^{10}$ and $R^{11}$, which may be identical or different, represent a linear or branched alkyl radical containing a number of carbon atoms ranging from 1 to 20, or a carboxyalkyl radical $—(CH_2)mCO_2H$ in which m=1 to 20;

the compounds of formula (VIII):

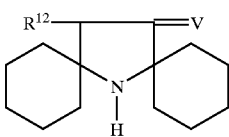
(VIII)

in which $R^{12}$ represents a hydrogen atom, a linear or branched alkyl residue containing a number of carbon atoms ranging from 1 to 20, or a $—C(O)NH_2$ radical, V=0; S, NH;

the compounds of formula (IX):

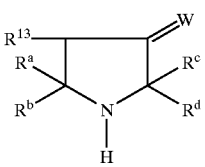
(IX)

in which $R^{13}$ has the same meaning as $R^2$ and W has the same meaning as V in formula (VIII):

the compounds of formula (X):

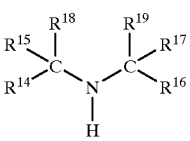
(X)

in which $R^{14}$, $R^{15}$, $R^{16}$, $R^{17}$, $R^{18}$ and $R^{19}$, which may be identical or different, represent a linear or branched alkyl radical containing a number of carbon atoms ranging from 1 to 20, a cycloalkyl radical containing at least 3 carbon atoms, a phenyl radical or a benzyl radical, or alternatively $R^{14}$ and $R^{15}$ form with the carbon atom which bears them, or alternatively $R^{16}$ and $R^{17}$ form with the carbon atom which bears them, a cycloalkyl containing a number of carbon atoms ranging from 3 to 10;

1,2,3,6-tetrahydro-2,2,6,6-tetramethylpyridine;

3,3-dimethyl-1-oxa-4-azaspiro[4.5]decane;

2,3,3,5,5-pentamethylmorpholine;

3,3,5,5-tetramethyl-2-methylenemorpholine;

N-(2,2,6,6-tetramethylpiperidyl-4)-ϵ-caprolactam;

4,4'-dimethylspiro(5α-cholestane-3,2'-oxazolidine)

the compounds of formula (XI):

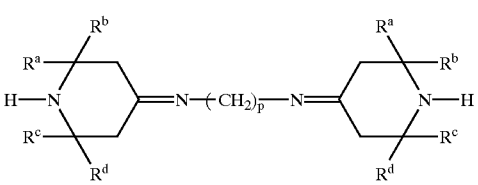
(XI)

with p=0 to 20;

the compounds of formula (XII):

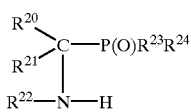
(XII)

in which $R^{20}$ and $R^{21}$, which may be identical or different, represent a hydrogen atom, a linear, branched or cyclic alkyl radical containing a number of carbon atoms ranging from 1 to 10, an aryl radical, or an aralkyl radical, or alternatively $R^{20}$ and $R^{21}$ are linked together so as to form a ring including the carbon atom bearing said radicals $R^{20}$ and $R^{21}$, said ring containing a number of carbon atoms, including the carbon bearing the radicals $R^{20}$ and $R^{21}$, ranging from 3 to 8; $R^{22}$ represents a linear or branched, saturated or unsaturated hydrocarbon-based radical which may comprise at least one ring, said radical containing a number of carbon atoms ranging from 1 to 30; $R^{23}$ and $R^{24}$, which may be identical or different, represent a linear or branched alkyl radical containing a number of carbon atoms ranging from 1 to 20, a cycloalkyl, aryl, alkoxy, aryloxy, aralkyloxy, perfluoroalkyl, aralkyl, dialkyl or diarylamino, alkylarylamino or thioalkyl radical, or alternatively $R^{23}$ and $R^{24}$ may also be linked together so as to form a ring including a phosphorus atom, said heterocycle possibly containing a number of carbon atoms ranging from 2 to 4 and also possibly containing one or more oxygen, sulfur or nitrogen atoms;

the oxa-1-diaza-oxo-spirodecanes of formula (XIII):

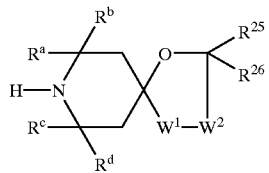
(XIII)

in which $W^1$ and $W^2$ are different and represent —C(O)— or —NH—, $R^{25}$ and $R^{26}$, which may be identical or different, represent a hydrogen atom, a linear or branched alkyl radical containing a number of carbon atoms ranging from 1 to 18, a phenyl radical, a naphthyl radical or a phenylalkyl radical, $R^{25}$ and $R^{26}$ may also form, together and with the carbon atom which bears them, a cycloalkyl containing a number of carbon atoms ranging from 5 to 12 or a 2,2,6,6-tetramethylpiperidyl radical;

the secondary polyamines represented by the general formula (XIV):

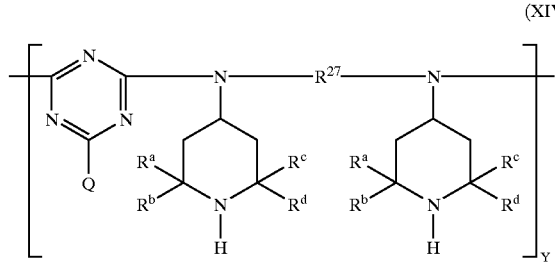
(XIV)

in which y=1 to 20, $R^{27}$ represents an alkylene radical containing a number of carbon atoms ranging from 2 to 12 which may be interrupted with an —O— or —$NR^{28}$—, $R^{28}$ denoting a hydrogen atom, an alkyl radical containing a number of carbon atoms ranging from 1 to 12, a cycloalkyl radical, Q represents a radical —$OR^{29}$, —$NHR^{30}$ or —$NR^{30}R^{31}$ in which $R^{29}$ represents a linear or branched alkyl radical containing a number of carbon atoms ranging from 1 to 12, a $C_3$–$C_{12}$ alkoxyalkyl radical, a cyclohexyl radical, a benzyl radical, a phenyl radical, a tolyl radical or a 2,2,6,6-tetrapiperidyl residue, $R^{30}$ and $R^{31}$ have the same meaning as $R^{29}$, $R^{30}$ and $R^{31}$ may also form, together and with the nitrogen atom which bears them, a 5—, 6— or 7-membered heterocyclic radical which may also contain an oxygen atom;

the secondary polyamine represented by formula (XV):

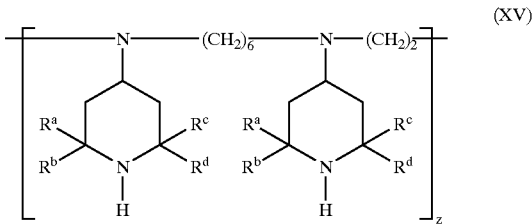
(XV)

in which z=1 to 200.

The present invention applies most particularly to the following secondary amines:

2,2,6,6-tetramethylpiperidine (formula (I) in which X=—$CH_2$— and $R^a$=$R^b$=$R^c$=$R^d$=—$CH_3$), 4-hydroxy-2,2,6,6-tetramethylpiperidine (formula (I) in which X=>CHZ with Z=OH and $R^a$=$R^b$=$R^c$=$R^d$=—$CH_3$), 4-oxo-2,2,6,6-tetramethylpiperidine (formula (I) in which X=—C(O)— and $R^a$=$R^b$=$R^c$=$R^d$=—$CH_3$), bis(2,2,6,6-tetramethylpiperidine) sebacate (formula (II) in which Y=—OC(O) $(CH_2)_8$ C(O)O and $R^a$=$R^b$=$R^c$=$R^d$=—$CH_3$), 2,2,3,4,5,5-hexamethylpyrrolidine (formula (III) in which $R^4$=$R^5$=—$CH_3$ and $R^a$=$R^b$=$R^c$=$R^d$=—$CH_3$), 2,2,4,5,5-pentamethyl-3-pyrrolidinylcarboxamide (formula (III) in which $R^4$=—$CH_3$, $R^5$=—$C(O)NH_2$ and $R^a$=$R^b$=$R^c$=$R^d$=—$CH_3$), 2,2,4,5,5-pentamethyl-3-pyrrolinylcarboxamide formula (IV) in which $R^6$=—$CH_3$, $R^7$=—$C(O)NH_2$ and $R^a$=$R^b$=$R^c$=$R^d$=—$CH_3$), the aminophosphates of formula (XII) in which $R^{20}$=—H, $R^{21}$=$(CH_3)_3C$—, $C_6H_{11}$—, $(CH_3)_2CH$—, $R^{22}$=$(CH_3)_3C$—, $C_6H_{11}$, $R^{23}$=$R^{24}$=$C_2H_5O$—, isopropoxy. Use will be made most particularly of diethyl 2,2-dimethyl-1-(1,1-dimethylamino)propylphosphonate, ($R^{20}$=H, $R^{21}$=$R^{22}$=$(CH_3)_3C$—, $R^{23}$=$R^{24}$=$C_2H_5O$—), 2,2,7,7,9,9-hexamethyl-1-oxa-4,8-diaza-3-oxospiro-[4.5] decane (formula XIII) in which $R^{25}$=$R^{26}$=—$CH_3$, W1=—NH— and W2=—C(O)—), 2,2,4,4-tetramethyl-3,20-diaza-7-oxa-21-oxo-dispiro [5.1.11.2]heneicosane sold by the company Hoechst under the name Hostavin® N-20 (formula (XIII) in which $R^{25}$ and $R^{26}$ form a —$(CH_2)_{11}$— ring, W1=C(O)—, W2=—NH— and $R^a$=$R^b$=$R^c$=$R^d$=—$CH_3$), the polyamine of formula (XIV) in which $R^{27}$=$(CH_2)_6$—, Q=NH-t$C_8H_{17}$ and $R^a$=$R^b$=$R^c$=$R^d$=$CH_3$, sold by the company Ciba-Geigy under the name Chimassorb® 944.

The examples which follow illustrate the invention.

The secondary amines used are:
2,2,6,6-tetramethylpiperidine,
bis(2,2,6,6-tetramethylpiperidine) sebacate,
diethyl 2,2-dimethyl-1-(1,1-dimethyl-ethylamino) propylphosphonate, obtained according to a method described in international patent application Wo 96/24620,
Chimassorb® 944 with a weight-average molecular mass equal to about 3 000.

The nitroxides obtained are identified by gas chromatography (GC), their melting points and mass spectrometry (MS). The magnetic mass spectra were recorded on a Micromass Autospec® mass spectrometer equipped with an atmospheric pressure ionization (API) source. The mass spectra were obtained by accumulation of x spectra (x should correspond to the time for loop injection of 20 μl directly into the API source).

EXAMPLE 1

Preparation of (2,2,6,6-tetramethyl-piperidine) N-oxide (TEMPO)

An organic solution consisting of 5 g of 2,2,6,6-tetramethylpiperidine (i.e. 0.0354 mol) dissolved in 20 ml of dichloromethane is prepared with stirring in a 100 ml round-bottomed flask fitted with 2 dropping funnels, a condenser, a pH-measuring probe and a stirrer. 20 ml of water are then added to this solution so as to have a two-phase system. Next, 10.8 g of a 40% solution of peracetic acid 4n acetic acid and aqueous 35% by weight $K_2CO_3$ solution are introduced (with stirring) slowly and simultaneously. The molar amount of peracetic acid introduced is 0.0568 mol, which corresponds to a peracetic acid/amine molar ratio of 1.6.

The amount of aqueous $K_2CO_3$ solution is adjusted such that the pH of the aqueous phase of the two-phase medium is maintained at between 7.2 and 7.5 in the course of the addition.

20 minutes after the addition, the total disappearance of the amine and the formation of TEMPO are found by gas chromatography (GC).

The reaction is stopped and $K_2CO_3$ solution is added so as to obtain a pH equal to 9, and the red-colored TEMPO is then extracted with $CH_2Cl_2$.

Evaporation of the solvent gives 4.9 g of TEMPO with a melting point equal to 36° C. The purity of the TEMPO is checked by GC relative to a sample of pure product (purity greater than 99%) sold by the company Aldrich.

Mass spectrum (m/e): 157 (M+1)

The yield of TEMPO relative to the amine used is 88%.

EXAMPLE 2

Preparation of bis(2,2,6,6-tetramethyl-peridine N-oxide) sebacate

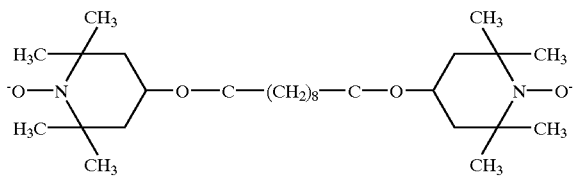

An organic solution consisting of 48 g of is(2,2,6,6-tetramethylpiperidine) sebacate, i.e. 0.10 mol, in 200 ml of $CH_2Cl_2$ is prepared with stirring n an assembly similar to that described in example 1 (reactor volume =500 ml). 50 ml of water are then added to this solution.

The two-phase mixture thus obtained is maintained under vigorous stirring.

71.2 ml of a 32% by weight solution of peracetic acid in acetic acid and a 35% by weight aqueous $K_2CO_3$ solution are then introduced, with stirring, slowly and simultaneously, so as to maintain the pH of the aqueous phase of the two-phase medium between 7.2 and 7.5.

After one hour, the reaction is stopped by raising the pH to 8.2.

The phases are allowed to separate by settling and the nitroxide is recovered by extraction with $CH_2Cl_2$.

Evaporation or the $CH_2Cl_2$ gives 49.6 g of a red solid with a melting point of 99.80° C. For this compound, Rozantsev, E. G. et al. (Izv. Adad. Nauk; S.S.S.R. Ser Khim. 572, 1965) give a melting point of 101° C. and the safety sheet of the product sold by the company Ciba-Geigy under the name CXA 5415 gives a melting point range of 95° C.–102° C.

Mass spectrum (m/e): 511 (M+1); 528 (N+18)

The yield of nitroxide relative to the diamine used is 97.3%.

EXAMPLE 3

Production of N-tert-butyl-l-diethyl-phosphono-2,2-dimethylpropyl nitroxide (referred to hereinbelow as 62-phosphorylated nitroxide) by oxidation of diethyl 2,2-dimethyl-1-(1,1-dimethylethylamino)-propylphosphonate (referred to hereinbelow as aminophosphonate)

5 g of aminophosphonate (0.017 mol) are diluted in 100 ml of ethyl acetate in a reactor equipped with two dropping funnels, a mechanical stirrer and a pH-measuring probe. 60 ml of water are added and the mixture is maintained under vigorous stirring. Next, 13.77 g of perpropionic acid at 20% by weight (0.0307 mol) in ethyl propionate and an 8.5% by weight aqueous $K_2CO_3$ solution (13 g of $K_2CO_3$ in 140 ml of water) are introduced, with stirring, slowly and simultaneously so as to maintain the pH of the aqueous phase of the two-phase medium between 5 and 7. An evolution of gas ($CO_2$) is observed. The solution gradually turns yellow and the active oxygen content of each phase is monitored regularly. After 16 hours, the organic phase is orange and the evolution of gas has entirely ceased. The organic phase is recovered after separation of the phases by settling, and the solvent is evaporated off. The crude nitroxide is in the form of a dark orange oil (4.6 g) with a purity equal to 62.5%. The yield of β-phosphorylated nitroxide is []57.5%.

Mass spectrum (mie):295 (M+1)

EXAMPLE 4

Oxidation of Chimassorb® 944 according to the present invention 11.1 g of Chimassorb® 944 are dissolved in 111 g of $CH_2Cl_2$ in the apparatus described in Example 2.

50 ml of water are then added to the solution obtained and the two-phase medium is kept stirring.

23.4 g of peracetic acid (as a 40% by weight solution in acetic acid) and 57.6 g of 35% by weight aqueous $K_2CO_3$ solution are added simultaneously over 20 minutes at room temperature, with stirring.

This addition takes place such that the pH of the aqueous phase is maintained between 7 and 7.5.

The reaction is exothermic despite an evolution of C$_2$.

At the end of the addition, the medium, which has turned orange-red, is kept stirring for 2 hours.

The stirring is then stopped and the phases are allowed to separate by settling for 15 hours.

The organic phase is recovered and the CH$_2$Cl$_2$ is evaporated off under reduced pressure. 10.7 g of a paramagnetic red solid are obtained. Yield: 91%.

What is claimed is:

1. A process for preparing a secondary amine N-oxide radicals (nitroxide radicals) from the corresponding secondary amine, comprising:

a/ dissolving the secondary amine with a water-immiscible organic solvent, and then adding water to form a two-phase medium having an organic phase and an aqueous phase, b/ adding simultaneously with vigorous stirring an amount of aliphatic peracid in a peracid/secondary amine molar ratio ranging from 1.5 to 2.5, and an amount of an aqueous basic solution sufficient to give the aqueous phase of the two-phase medium a pH reading from 4 to 12, at a temperature of between −10° C. and +40° C., until conversion of the secondary amine is complete, and then c/ recovering the organic phase by separation of the phases by settling, and isolating the nitroxide by evaporating the organic solvent under reduced pressure.

2. A process as claimed in claim 1, wherein the pH of the aqueous phase of the two-phase medium ranges from 5 to 9.

3. A process as claimed in claim 1, wherein the temperature is between −5° C. and +30° C.

4. A process as claimed in claim 1, wherein the organic solvent is chosen from aliphatic and cycloaliphatic hydrocarbons, aromatic hydrocarbons, chlorinated hydrocarbons and aliphatic acid esters.

5. A process as claimed in claim 1, wherein the peracid/secondary amine molar ratio ranges from 1.5 to 2.

6. A process as claimed in claim 4, wherein the aliphatic hydrocarbons are pentane, hexane or heptane, the chlorinated hydrocarbons are methylene chloride or 1,2-dichloroethane, and the aliphatic acid esters are ethyl acetate or ethyl propionate.

7. A process as claimed in claim 1, wherein the aliphatic peracid is peracetic acid, perpropionic acid or perbutanoic acid.

8. A process as claimed in claim 1, wherein the aqueous basic solution is an aqueous solution of a carbonate or hydrogen carbonate of an alkali metal or of an alkaline-earth metal.

9. A process as claimed in claim 8, wherein the alkali metal carbonate or hydrogen carbonate is NaHCO$_3$, KHCO$_3$ or Na$_2$CO$_3$.

10. A process as claimed in claim 1, wherein the secondary amine is chosen from the compounds represented by the formulae below in which R$^a$, R$^b$, R$^c$ and R$^d$, which may be identical or different, represent a linear or branched alkyl radical containing 1 to 10 carbon atoms, or R$^a$ and R$^b$ form with the carbon atom which bears them, or R$^c$ and R$^d$ form with the carbon atom which bears them, a cycloalkyl containing 3 to 10 carbon atoms or a spiran, cholestane or androstane residue:

the compounds of formula (1):

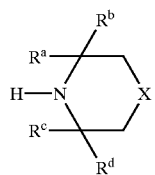
(I)

wherein

X is a divalent radical chosen from the following radicals:

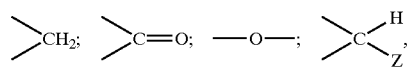

Z is a monovalent residue chosen from —CN, —NHR, —OR, —N=C(R)$_2$ a benzyl radical, a phenyl radical, —CN, —C(O)R$^1$;

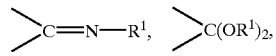

R is a hydrogen atom, a linear or branched alkyl radical containing 1 to 10 carbon atoms is;

the compounds of formula (II):

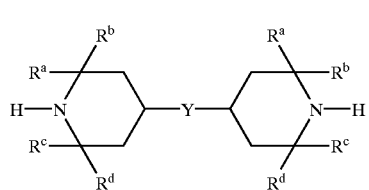
(II)

wherein

Y is a divalent residue chosen from:
OC(O)-(CR$^2$R$^3$)$_n$-C(O)O—,
NH-(CR$^2$R$^3$)$_n$NH—,
NHC(O)-(CR$^2$R$^3$)$_n$-C(O)NH,
S—, and —O—, R$^2$ and R$^3$, which may be identical or different, are each a hydrogen atom or a linear or branched alkyl radical containing 1 to 10 carbon atoms, and n is an integer ranging from 0 to 20;

the compounds of formula (III):

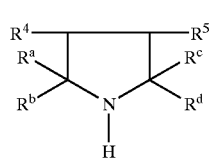
(III)

wherein

R$^4$ is a hydrogen atom or a linear or branched alkyl radical containing 1 to 10 carbon atoms, and R$^5$ is a hydrogen atom, —CH$_3$, —C$_2$H$_5$, —CH$_2$OH, —C(O)NH$_2$, —OH or —CHO;

the compounds of formula (IV):

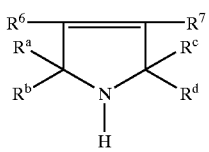

(IV)

wherein
$R^6$ has the same meaning as $R^4$, and
$R^7$ has the same meaning as $R^5$,
the 1,1,3,3,-tetramethylpyrrolopyridines of formula (V):

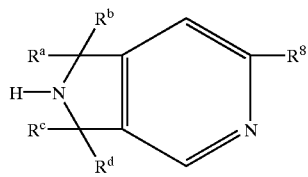

(V)

and the 1,1,3,3,-tetramethyl-2,3-dihydroisoindoles of formula (VI):

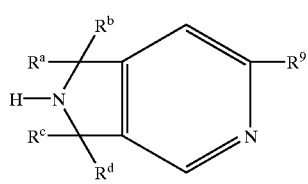

(VI)

wherein
$R^8$ and $R^9$ are each a hydrogen atom or a linear or branched alkyl radical containing 1 to 10 carbon atoms;
the compounds of formula (VII):

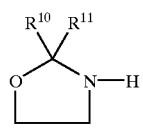

(VII)

wherein
$R^{10}$ and $R^{11}$, which may be identical or different, are each a linear or branched alkyl radical containing 1 to 10 carbon atoms, or a carboxyalkyl radical —$(CH_2)mCO_2H$, and m is 1 to 20;
the compounds of formula (VIII):

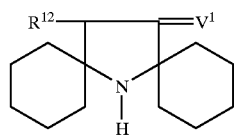

(VIII)

wherein
$R^{12}$ is a hydrogen atom, a linear or branched alkyl residue containing 1 to 20 carbon atoms, or a —$C(O)NH_2$ radical, and $V^1$ is NH;
the compounds of formula (IX):

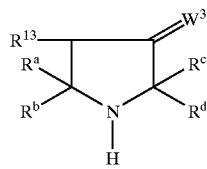

(IX)

wherein
$R^{13}$ has the same meaning as $R^{12}$, and
$W^3$ has the same meaning as $V^1$;
the compounds of formula (X):

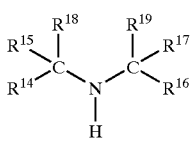

(X)

wherein
$R^{14}$, $R^{15}$, $R^{16}$, $R^{17}$, $R^{18}$ and $R^{19}$, which may be identical or different, are each a linear or branched alkyl radical containing 1 to 20 carbon atoms, a cycloalkyl radical containing at least 3 carbon atoms, a phenyl radical or a benzyl radical, or alternatively $R^{14}$ and $R^{15}$ form with the carbon atom which bears them, or alternatively $R^{16}$ and $R^{17}$ form with the carbon atom which bears them, a cycloalkyl containing a number of carbon atoms ranging from 3 to 10;

1,2,3,6-tetrahydro-2,2,6,6-tetramethylpyridine;
3,3-dimethyl-1-oxa-4-azaspiro decane;
2,3,3,5,5-pentamethylmorpholine;
3,3,5,5-tetramethyl-2-methylenemorpholine;
N-(2,2,6,6-tetramethylpiperidyl-4)-ε-caprolactam;
4,4'-dimethylspiro(5α-cholestane-3,2-oxazolidine);
the compounds of formula (XI):

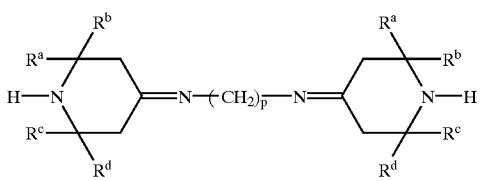

(XI)

wherein
p is 0 to 20;
the compounds of formula (XII):

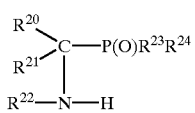

(XII)

wherein
$R^{20}$ and $R^{21}$, which may be identical or different, are each a hydrogen atom, a linear, branched or cyclic alkyl radical containing 1 to 10 carbon atoms, an aryl radical, or an aralkyl radical, or alternatively $R^{20}$ and $R^{21}$ are linked together so as to form a ring including the carbon atom bearing said radicals $R^{20}$ and $R^{21}$, said ring containing a number of carbon atoms, including the carbon bearing the radicals $R^{20}$ and $R^{21}$, $R^{22}$ is a linear or branched, saturated or unsaturated hydrocarbon-based radical which may comprise at least one ring, said radical containing 1 to 30 carbon atoms, and $R^{23}$ and $R^{24}$, which may be identical or different, are each a linear or branched alkyl radical containing 1 to 20 carbon atoms, a cycloalkyl, aryl, alkoxy, aryloxy, aralkyloxy, perfluoroalkyl, aralkyl, dialkyl or diarylamino, alkylarylamino or thioalkyl radical, or alternatively $R^{23}$ and $R^{24}$ are linked together so as to form a heterocycle ring including a phosphorus atom, said heterocycle ring containing 2 to 4 carbon atoms and also optionally containing one or more oxygen, sulfur or nitrogen atoms;

the oxa-1-diaza-oxo-spirodecanes of formula (XIII):

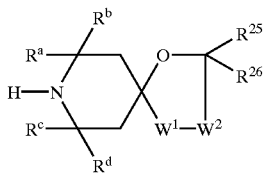

(XIII)

wherein $W^1$ and $W^2$ are different and are each —C(O)— or —NH—, f $R^{25}$ and $R^{26}$, which may be identical or different, are each a hydrogen atom, a linear or branched alkyl radical containing 1 to 18 carbon atoms, a phenyl radical, a naphthyl radical or a phenylalkyl radical, or alternatively $R^{25}$ and $R^{26}$ form, together with the carbon atom which bears them, a cycloalkyl containing 5 to 12 carbon atoms ranging from 5 to 12 or a 2,2,6,6-tetramethylpiperidyl radical;

the secondary polyamines of formula (XIV):

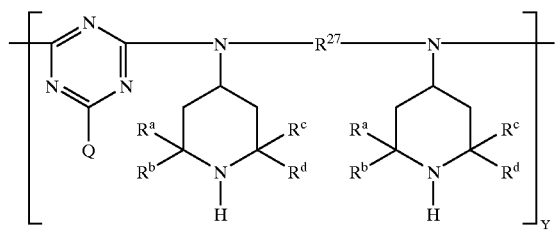

(XIV)

wherein y is 1 to 20, $R^{27}$ is an alkylene radical containing 2 to 12 carbon atoms which may be interrupted with an —O— or —$NR^{28}$—, $R^{28}$ is a hydrogen atom, an alkyl radical containing 1 to 12 carbon atoms, or a cycloalkyl radical, Q is a radical —$OR^{29}$, —$NHR^{30}$ or —$NR^{30}R^{31}$, $R^{29}$ is a linear or branched alkyl radical containing 1 to 12 carbon atoms, a $C_3$–$C_{12}$ alkoxyalkyl radical, a cyclohexyl radical, a benzyl radical, a phenyl radical, a tolyl radical or a 2,2,6,6-tetramethylpiperidyl residue, $R^{30}$ and $R^{31}$ have the same meaning as $R^{29}$, or alternatively $R^{30}$ and $R^{31}$ form, together with the nitrogen atom which bears them, are a 5—, 6— or 7-membered heterocyclic radical which may also contain an oxygen atom;

the secondary polyamines of formula (XV):

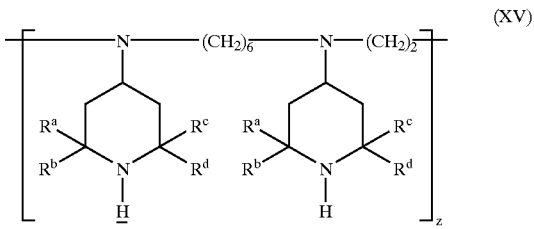

(XV)

wherein z is 1 to 200.

11. A process as claimed in claim 10, wherein the secondary amine is:

2,2,6,6-tetramethylpiperidine, 4-hydroxy-2,2,6,6-tetramethylpiperidine, 4-oxo-2,2,6,6-tetramethylpiperidine, bis(2,2,6,6-tetramethylpiperidine) sebacate, 2,2,3,4,5,5-hexamethylpyrrolidine, 2,2,4,5,5-pentamethyl-3-pyrrolidinylcarboxamide, 2,2,4,5,5-pentamethyl-3-pyrrolinylcarboxamide, diethyl 2,2-dimethyl- 1 -(I, I -dimethylamino) propylphosphonate, 2,2,7,7,9,9-hexamethyl- 1 -oxa-4,8-diaza-3-oxospiro[4.5] decane, 2,2,4,4-tetramethyl-3,20-diaza-7-oxa-2 1 -oxodispiro [5.1.11 .2]heneicosane, or the polyamine of formula (XIV) in which $R^{27}$=—$(CH_2)_6$—, Q=NH-t$C_8H_{17}$ and $R^a$=$R^b$=$R^c$=$R^d$=—$CH_3$.

12. A process as claimed in claim 10, wherein the peracid/secondary amine molar ratio ranges from 1.5 to 2.

13. A process as claimed in claim 10, wherein the pH of the aqueous phase of the two-phase medium ranges from 5 to 9.

14. A process as claimed in claim 10, wherein the temperature is between −5° C. and +30° C.

15. A process as claimed in claim 1, wherein the organic solvent is chosen from aliphatic and cycloaliphatic hydrocarbons, aromatic hydrocarbons, chlorinated hydrocarbons and aliphatic acid esters.

16. A process as claimed in claim 15, wherein the aliphatic hydrocarbons are pentane, hexane or heptane, the chlorinated hydrocarbons are methylene chloride or 1,2-dichloroethane, and the aliphatic acid esters are ethyl acetate or ethyl propionate.

17. A process as claimed in claim 10, wherein the aliphatic peracid is peracetic acid, perpropionic acid or perbutanoic acid.

18. A process as claimed in claim 10, wherein the aqueous basic solution is an aqueous solution of a carbonate or hydrogen carbonate of an alkali metal or of an alkaline-earth metal.

19. A process as claimed in claim 18, wherein the alkali metal carbonate or hydrogen carbonate is $NaHCO_3$, $KHCO_3$ or $Na_2CO_3$.

* * * * *

UNITED STATES PATENT AND TRADEMARK OFFICE
CERTIFICATE OF CORRECTION

PATENT NO. : 6,538,141 B1
DATED : March 25, 2003
INVENTOR(S) : Jean-Philippe Gillet et al.

It is certified that error appears in the above-identified patent and that said Letters Patent is hereby corrected as shown below:

Column 11,
Line 56, after "$KHCO_3$" insert -- ,$K_2CO_3$ --.

Column 12,
Line 25, after "$R^1$", insert -- or --.
Line 29, after "atoms" insert -- , $R^1$ has the same meaning as R, -- and delete "is;"

Column 14,
Line 1, after "is" insert -- O, S or --.

Column 15,
Line 4, after "containing" insert -- 3 to 8 -- and delete "a number of".
Line 32, after "–NH–," delete "f".
Line 39, after "atoms" delete "ranging from 5 to 12".

Column 16,
Line 28, after "2,2,4,5," insert -- 5 -- and delete "$^5$".
Line 30, after "(" insert -- 1,1 -- and delete "l,l".
Line 35, after "-oxa-" insert -- 21 -- and delete "2 1".

Signed and Sealed this

Second Day of March, 2004

JON W. DUDAS
*Acting Director of the United States Patent and Trademark Office*